(12) United States Patent
Plachetka (10) Patent No.: US 6,926,907 B2
(45) Date of Patent: Aug. 9, 2005

(54) PHARMACEUTICAL COMPOSITIONS FOR THE COORDINATED DELIVERY OF NSAIDS

(75) Inventor: John R. Plachetka, Chapel Hill, NC (US)

(73) Assignee: Pozen Inc., Chapel Hill, NC (US)

(*) Notice: Subject to any disclaimer, the term of this patent is extended or adjusted under 35 U.S.C. 154(b) by 273 days.

(21) Appl. No.: 10/158,216

(22) Filed: May 31, 2002

(65) Prior Publication Data

US 2003/0069255 A1 Apr. 10, 2003

Related U.S. Application Data

(60) Provisional application No. 60/294,588, filed on Jun. 1, 2001.

(51) Int. Cl.$^7$ .............................. A61K 9/22; A61K 9/24; A61K 9/32; A61K 9/52
(52) U.S. Cl. ....................... 424/472; 424/457; 424/463; 424/468; 424/474; 424/480; 424/482
(58) Field of Search ................................ 424/457, 463, 424/468, 472, 474, 480, 482, 464, 451

(56) References Cited

U.S. PATENT DOCUMENTS

| 4,255,431 A | 3/1981 | Junggren et al. | 424/263 |
|---|---|---|---|
| 4,508,905 A | 4/1985 | Junggren et al. | 546/271 |
| 4,554,276 A | 11/1985 | LaMattina | 514/272 |

(Continued)

FOREIGN PATENT DOCUMENTS

| DE | 198 01 811 A1 | 1/1998 | ............ A61K/9/50 |
|---|---|---|---|
| EP | 0 320 550 A1 | 6/1989 | ........... A61K/33/08 |
| EP | 0 426 479 B1 | 5/1991 | .......... A61K/31/415 |

(Continued)

OTHER PUBLICATIONS

Howden, "Clinical Pharmacology of Omeprazole," *Clin. Pharmacokinet.* 20(1):38–49 (1991) abstract.
Pilbrant, et al., "Development of an Oral Formulation of Omeprazole," *Scand. J. Gastroenterol.* 20(Suppl. 108):113–120 (1985).
Sharma, "Comparison of 24–Hour Intragastric pH Using Four Liquid Formulations of Lansoprazole and Omeprazole," *Am. J. Health–Syst. Pharm.* 56(Supp. 4):S18–S21 (1999).

(Continued)

*Primary Examiner*—James M. Spear
(74) *Attorney, Agent, or Firm*—Michael A. Sanzo; Fitch, Even, Tabin & Flannery (57) ABSTRACT

The present invention is directed to drug dosage forms that release an agent that raises the pH of a patient's gastrointestinal tract, followed by a non-steroidal anti-inflammatory drug. The dosage form is designed so that the NSAID is not released until the intragastric pH has been raised to a safe level. The invention also encompasses methods of treating patients by administering this coordinated release, gastroprotective, antiarthritic/analgesic combination unit dosage form to achieve pain and symptom relief with a reduced risk of developing gastrointestinal damage such as ulcers, erosions and hemorrhages.

55 Claims, 2 Drawing Sheets

U.S. PATENT DOCUMENTS

| | | | |
|---|---|---|---|
| 4,562,261 A | 12/1985 | Hirata et al. | 548/184 |
| 4,619,934 A | 10/1986 | Sunshine et al. | 514/277 |
| 4,676,984 A | 6/1987 | Wu et al. | 424/157 |
| 4,704,278 A | 11/1987 | Wu et al. | 424/157 |
| 4,757,060 A | 7/1988 | Lukacsko et al. | 514/160 |
| 4,766,117 A | 8/1988 | Crawford et al. | 514/219 |
| 4,786,505 A | 11/1988 | Lovgren et al. | 424/468 |
| 4,965,065 A | 10/1990 | Lukacsko et al. | 424/10 |
| 5,037,815 A | 8/1991 | Lukacsko et al. | 514/162 |
| 5,043,358 A | 8/1991 | Lukacsko et al. | 514/653 |
| 5,204,118 A | 4/1993 | Goldman et al. | 424/489 |
| 5,260,333 A | 11/1993 | Lukacsko et al. | 514/471 |
| 5,364,616 A | 11/1994 | Singer et al. | 424/52 |
| 5,373,022 A | 12/1994 | Fawzi et al. | 514/570 |
| 5,417,980 A | 5/1995 | Goldman et al. | 424/464 |
| 5,466,436 A | 11/1995 | Stables | 514/161 |
| 5,514,663 A | 5/1996 | Mandel | 514/33 |
| 5,631,022 A | 5/1997 | Mandel et al. | 424/456 |
| 5,643,960 A | 7/1997 | Breitner et al. | 514/570 |
| 5,686,105 A | 11/1997 | Kelm et al. | 424/452 |
| 5,716,648 A | 2/1998 | Halskov et al. | 424/682 |
| 5,955,451 A | 9/1999 | Lichtenberger et al. | 514/78 |
| 6,013,281 A | 1/2000 | Lundberg et al. | 424/468 |
| 6,025,395 A | 2/2000 | Breitner et al. | 514/570 |
| 6,160,020 A | 12/2000 | Ohannesian et al. | 514/629 |
| 6,162,816 A | 12/2000 | Bohlin et al. | 514/338 |
| 6,207,188 B1 | 3/2001 | Gustavsson et al. | 424/464 |
| 6,365,184 B1 | 4/2002 | Depui et al. | 424/469 |
| 6,395,298 B1 | 5/2002 | Flanagan et al. | 424/479 |
| 6,485,747 B1 | 11/2002 | Flanagan et al. | 424/479 |
| 6,544,556 B1 | 4/2003 | Chen et al. | 424/469 |
| 2001/0025107 A1 | 9/2001 | Barberich et al. | 546/273.7 |
| 2001/0036473 A1 | 11/2001 | Scott et al. | 424/463 |
| 2001/0044410 A1 | 11/2001 | Gelber et al. | 514/27 |
| 2002/0012676 A1 | 1/2002 | Lundberg et al. | 424/400 |
| 2002/0042433 A1 | 4/2002 | Yelle et al. | 514/338 |
| 2002/0044962 A1 | 4/2002 | Cherukuri et al. | 424/459 |
| 2002/0045184 A1 | 4/2002 | Chen | 435/6 |
| 2002/0086029 A1 | 7/2002 | Lundberg et al. | 424/184.1 |
| 2002/0111370 A1 | 8/2002 | Bergman et al. | 514/338 |
| 2002/0155153 A1 | 10/2002 | Depui et al. | 424/452 |
| 2003/0008903 A1 | 1/2003 | Barberich et al. | 514/338 |
| 2003/0113375 A1 | 6/2003 | Lundberg et al. | 424/474 |
| 2003/0129235 A1 | 7/2003 | Chen et al. | 424/470 |

FOREIGN PATENT DOCUMENTS

| | | | | |
|---|---|---|---|---|
| EP | 0 426 479 A1 | 5/1991 | | A61K/31/415 |
| EP | 0 550 083 B1 | 7/1993 | | A61K/31/34 |
| GB | 2 105 193 | 3/1983 | | A61K/31/34 |
| WO | WO 85/03443 | 8/1985 | | A61K/45/06 |
| WO | WO 93/12817 | 7/1993 | | A61K/45/06 |
| WO | WO 94/07541 | 4/1994 | | A61K/49/00 |
| WO | WO 98/22117 | 5/1998 | | A61K/33/24 |
| WO | WO 99/00380 | 1/1999 | | C07D/401/12 |
| WO | WO 99/12524 | 3/1999 | | A61K/9/20 |
| WO | WO 00/71122 | 11/2000 | | A61K/31/44 |
| WO | WO 00/72838 A1 | 12/2000 | | A61K/31/04 |
| WO | WO 03/017980 A1 | 3/2003 | | A61K/9/16 |

OTHER PUBLICATIONS

Bigard, et al., "Complete Prevention by Omeprazole of Aspirin Induced Gastric Lesions in Healthy Subjects," *GUT* 29(5):A712, T49 (1988).

Bombardier, et al., "Comparison of Upper Gastrointestinal Toxicity of Rofecoxib and Naproxen in Patients with Rheumatoid Arthritis," *N. Engl. J. Med.* 343:1520–1528 (2000).

Brown, et al., "Prevention of the Gastrointestinal Adverse Effects of Nonsteroidal Anti–Inflammatory Drugs," *Pract. Drug Safety 21*:503–512 (1999).

Cullen, et al., "Primary Gastroduodenal Prophylaxis with Omeprazole for Non–Steroidal Anti–Inflammatory Drug Users," *Aliment. Pharmacol. Ther. 12*:135–140 (1998).

Hawkey, "Progress in Prophylaxis Against Nonsteroidal Anti–Inflammatory Drug–Associated Ulcers and Erosions," *Am. J. Med.* 104:67S–74S (1998).

Hawkey, et al., "Omeprazole Compared with Misoprostol for Ulcers Associated with Nonsteroidal Anti–Inflammatory Drugs," *N. Engl. J. Med.* 338:727–734 (1998).

Katz, et al., "Gastric Acidity and Acid Breakthrough with Twice–Daily Omeprazole or Iansoprazole," *Aliment. Pharmacol. Ther* 14:709–714 (2000).

Kephart, et al., "Coprescribing of Nonsteroidal Anti–Inflammatory Drugs and Cytoprotective and Antiulcer Drugs in Nova Scotia's Senior Population," *Clin. Ther.* 17:1159–1173 (1995).

Lad, et al., "Management of Nonsteroidal Anti–Inflammatory Drug–Induced Gastroduodenal Disease by Acid Suppression," *Can. J. Gastroenterol* 13:135–142 (1999).

Mattsson, et al., "Omeprazole Provides Protection Against Experimentally Induced Gastric Mucosal Lesions," *Eur. J. Pharmacol.* 91:111–114 (1983).

Oddsson, et al., "Endoscopic Findings in the Stomach and Duodenum after Treatment with Enteric–Coated and Plain Naproxen Tablets in Healthy Subjects," *Scand. J. Gastroenterol.* 25:231–234 (1990).

Scheiman, "NSAID–Induced Peptic Ulcer Disease: A Critical Rview of Pathogenesis and Management," *Dig. Dis.* 12:210–222 (1994).

Selway, "Potential Hazards of Long–Term Acid Suppression," *Scand. J. Gasatroenterol.* 25(Supp. 178):85–92 (1990).

Silverstein, et al., "Gastrointestinal Toxicity with Celecoxib vs. Nonsteroidal Anti–Inflammatory Drugs for Osteoarthritis and Rheumatoid Arthritis; The CLASS Study: A Randomized Controlled Trial," *JAMA* 284:1247–1255 (2000).

Tronstad, et al., "Gastroscopic Findings after Treatment with Enteric–Coated and Plain Naproxen Tablets in Healthy Subjects," *Scand. J. Gastroenterol.* 20:239–242 (1985).

Wolfe, et al., "Gastrointestinal Toxicity of Nonsteroidal Anti–Inflammatory Drugs," *N. Engl. J. Med.* 340:1888–1899 (1999).

Yeomans, et al., "A Comparison of Omeprazole with Ranitidine for Ulcers Associated with Nonsteroidal Anti–Inflammatory Drugs," *N. Engl. J. Med.* 338:719–726 (1998).

Yeomans, et al., "New Data on Healing of Nonsteroidal Anti–Inflammatory Drug–Associated Ulcers and Erosions," *Am. J. Med.* 104:56S–61S (1998).

English language abstract for DE 198 01 811, Reference B13 above.

Dent, "Why Proton Pump Inhibition Should Heal and Protect Against Nonsteroidal Anti–Inflammatory Drug Ulcers," *Am. J. Med.* 104:52S–55S (1998).

Kimmey, et al., "Role of $H_2$–Receptor Blockers in the Prevention of Gastric Injury Resulting from Nonsteroidal Anti–inflammatory Agents," *Am. J. Med.* 84:49–52 (1988).

Lee, et al., "Omeprazole Prevents Indomethacin–Induced Gastric Ulcers in Rabbits," *Aliment. Pharmacol. Ther.* 10:571–576 (1996).

Lichtenbergetr, et al., "Nonsteroidal Anti–inflammatory Drug and Phospholipid Prodrugs: Combination Therapy with Antisecretory Agents in Rats," *Gastroenterology* 111:990–995 (1996).

Savarino, et al., "Effect of One–Month Treatment with Nonsteroidal Antiinflammatory Drugs (NSAIDs) on Gastric pH of Rheumatoid Arthritis Patients," *Digestive Diseases and Sciences* 43:459–463 (1998).

Wagner, et al., "Effects of Nonsteroidal Antiinflammatory Drugs on Ulcerogenesis and Gastric Secretion in Pylorus–Ligated Rat," *Digestive Diseases and Sciences* 40:134–140 (1995).

PHARMACEUTICAL COMPOSITIONS FOR THE COORDINATED DELIVERY OF NSAIDS

CROSS REFERENCE TO RELATED APPLICATIONS

The present application claims priority to U.S. provisional application No. 60/294,588, filed on Jun. 1, 2001.

FIELD OF THE INVENTION

The present invention is directed to pharmaceutical compositions that provide for the coordinated release of an acid inhibitor and a non-steroidal anti-inflammatory drug (NSAID). These compositions have a reduced likelihood of causing unwanted side effects, especially gastrointestinal side effects, when administered as a treatment for pain, arthritis and other conditions amenable to treatment with NSAIDs.

BACKGROUND OF THE INVENTION

Although non-steroidal anti-inflammatory drugs are widely accepted as effective agents for controlling pain, their administration can lead to the development of gastroduodenal lesions, e.g., ulcers and erosions, in susceptible individuals. It appears that a major factor contributing to the development of these lesions is the presence of acid in the stomach and upper small intestine of patients. This view is supported by clinical studies demonstrating an improvement in NSAID tolerability when patients are also taking independent doses of acid inhibitors (*Dig. Dis.* 12:210–222 (1994); *Drug Safety* 21:503–512 (1999); *Aliment. Pharmacol. Ther.* 12:135–140 (1998); *Am. J. Med.* 104(3A):67S–74S (1998); *Clin. Ther.* 17:1159–1173 (1995)). Other major factors contributing to NSAID-associated gastropathy include a local toxic effect of NSAIDs and inhibition of protective prostaglandins (*Can. J. Gastroenterol.* 13:135–142 (1999) and *Pract. Drug Safety* 21:503–512, (1999)), which may also make some patients more susceptible to the ulcerogenic effects of other noxious stimuli.

In general, more potent and longer lasting acid inhibitors, such as proton pump inhibitors, are thought to be more protective during chronic administration of NSAIDs than shorter acting agents, e.g., histamine $H_2$ receptor antagonists (H-2 blockers) (*N. Eng. J. Med.* 338:719–726 (1998); *Am. J. Med.* 104(3A):56S–61S (1998)). The most likely explanation for this is that gastric pH fluctuates widely throughout the dosing interval with short acting acid inhibitors leaving the mucosa vulnerable for significant periods of time. In particular, the pH is at its lowest point, and hence the mucosa is most vulnerable, at the end of the dosing interval (least amount of acid inhibition) and for some time after the subsequent dose of acid inhibitor. In general, it appears that when a short acting acid inhibitor and an NSAID are administered simultaneously, NSAID-related mucosal damage occurs before the pH of the gastrointestinal tract can be raised and after the acid inhibiting effect of the short acting acid inhibitor dissipates.

Although longer lasting agents, such as proton pump inhibitors (PPIs), usually maintain a consistently higher gastroduodenal pH throughout the day, after several days dosing, their antisecretory effect may be delayed for several hours and may not take full effect for several days (*Clin. Pharmacokinet.* 20:38–49 (1991)). Their effect may be diminished toward the end of the usual dosing interval. Intragastric pH rises particularly slowly with the first dose in a course of treatment since this class of drugs is enteric coated to avoid destruction by stomach acid. As a result, absorption is delayed for several hours. Even then, some patients fail to respond consistently to drugs of this type and suffer from "acid breakthrough" which again leaves them vulnerable to NSAID-associated gastroduodenaldamage (*Aliment. Pharmacol. Ther.* 14:709–714 (2000)). Despite a significant reduction in gastroduodenal lesions with the concomitant administration of a proton pump inhibitor during six months of NSAID therapy, up to 16% of patients still develop ulcers, indicating that there remains substantial room for improvement (*N. Eng. J. Med.* 338:727–734 (1998)). Thus, the addition of a pH sensitive enteric coating to an NSAID could provide additional protection against gastroduodenal damage not provided by the H2 blocker or PPI alone. In addition, although long acting acid inhibitors may reduce the risk of GI lesions in chronic NSAID users, there are questions about the safety of maintaining an abnormally elevated pH in a patient's GI tract for a prolonged period of time (*Scand. J. Gastroenterol. Suppl.* 178:85–92 (1990)).

Recognizing the potential benefits of PPIs for the prevention of NSAID-induced gastroduodenal damage, others have disclosed strategies for combining the two active agents for therapeutic purposes. However, these suggestions do not provide for coordinated drug release or for reducing intragastric acid levels to a non-toxic level prior to the release of NSAID (U.S. Pat. Nos. 5,204,118; 5,417,980; 5,466,436; and 5,037,815). In certain cases, suggested means of delivery would expose the gastrointestinal tract to NSAIDs prior to onset of PPI activity (U.S. Pat. No. 6,365,184).

Attempts to develop NSAIDs that are inherently less toxic to the gastrointestinal tract have met with only limited success. For example, the recently developed cyclooxygenase-2 (COX-2) inhibitors show a reduced tendency to produce gastrointestinal ulcers and erosions, but a significant risk is still present, especially if the patient is exposed to other ulcerogens (*JAMA* 284:1247–1255 (2000); *N. Eng. J. Med.* 343:1520–1528 (2000)). In this regard, it appears that even low doses of aspirin will negate most of the benefit relating to lower gastrointestinal lesions. In addition, the COX-2 inhibitors may not be as effective as other NSAIDs at relieving some types of pain and have been associated with significant cardiovascular problems (*JADA* 131:1729–1737 (2000); *SCRIP* 2617, pg. 19, Feb. 14, 2001); NY Times, May 22, 2001, pg. C1)).

Other attempts to produce an NSAID therapy with less gastrointestinal toxicity have involved the concomitant administration of a cytoprotective agent. In 1998, Searle began marketing Arthrotec™ for the treatment of arthritis in patients at risk for developing GI ulcers. This product contains misopristol (a cytoprotective prostaglandin) and the NSAID diclofenac. Although patients administered Arthrotec™ do have a lower risk of developing ulcers, they may experience a number of other serious side effects such as diarrhea, severe cramping and, in the case of pregnant women, potential damage to the fetus.

Another approach has been to produce enteric coated NSAID products. However, even though these have shown modest reductions in gastroduodenal damage in short term studies (*Scand. J. Gastroenterol.* 20: 239–242 (1985) and *Scand. J. Gastroenterol.* 25:231–234 (1990)), there is no consistent evidence of a long term benefit during chronic treatment.

Overall, it may be concluded that the risk of inducing GI ulcers is a recognized problem associated with the administration of NSAIDs and that, despite considerable effort, an ideal solution has not yet been found.

SUMMARY OF THE INVENTION

The present invention is based upon the discovery of a new method for reducing the risk of gastrointestinal side effects in people taking NSAIDs for pain relief and for other conditions, particularly during chronic treatment. The method involves the administration of a single, coordinated, unit-dose product that combines: a) an agent that actively raises intragastric pH to levels associated with less risk of NSAID-induced ulcers; and b) an NSAID that is specially formulated to be released in a coordinated way that minimizes the adverse effects of the NSAID on the gastroduodenal mucosa. Either short or long acting acid inhibitors can be effectively used in the dosage forms. This method has the added benefit of being able to protect patients from other gastrointestinal ulcerogens whose effect may otherwise be enhanced by the disruption of gastroprotective prostaglandins due to NSAID therapy.

In its first aspect, the invention is directed to a pharmaceutical composition in unit dosage form suitable for oral administration to a patient. The composition contains an acid inhibitor present in an amount effective to raise the gastric pH of a patient to at least 3.5, preferably to at least 4, and more preferably to at least 5, when one or more unit dosage forms are administered. The gastric pH should not exceed 7.5 and preferably should not exceed 7.0. The term "acid inhibitor" refers to agents that inhibit gastric acid secretion and increase gastric pH. In contrast to art teaching against the use of H2 blockers for the prevention of NSAID-associated ulcers (*N. Eng. J. Med.* 340: 1888–1899 (1999)), these agents are preferred compounds in the current invention. Specific, H2 blockers that may be used include cimetidine, ranitidine, ebrotidine, pabutidine, lafutidine, loxtidine or famotidine. The most preferred acid inhibitor is famotidine present in dosage forms in an amount of between 5 mg and 100 mg. Other agents that may be effectively used include proton pump inhibitors such as omeprazole, esomeprazole, pantoprazole, lansoprazole or rabeprazole.

The pharmaceutical composition also contains a nonsteroidal anti-inflammatory drug in an amount effective to reduce or eliminate pain or inflammation. The NSAID may be a COX-2 inhibitor such as celecoxib, rofecoxib, meloxicam, piroxicam, valdecoxib, parecoxib, etoricoxib, CS-502, JTE-522, L-745,337 or NS398. Alternatively, the NSAID may be aspirin, acetaminophen, ibuprofen, flurbiprofen, ketoprofen, naproxen, oxaprozin, etodolac, indomethacin, ketorolac, lornoxicam, nabumetone, or diclofenac. The most preferred NSAID is naproxen in an amount of between 50 mg and 1500 mg, and more preferably, in an amount of between 200 mg and 600 mg. It will be understood that, for the purposes of the present invention, reference to an acid inhibitor, NSAID, or analgesic agent will include all of the common forms of these compounds and, in particular, their pharmaceutically acceptable salts. The amounts of NSAIDs which are therapeutically effective may be lower in the current invention than otherwise found in practice due to potential positive kinetic interaction and NSAID absorption in the presence of an acid inhibitor.

The term "unit dosage form" as used herein refers to a single entity for drug administration. For example, a single tablet or capsule combining both an acid inhibitor and an NSAID would be a unit dosage form. A unit dosage form of the present invention preferably provides for coordinated drug release, in a way that elevates gastric pH and reduces the deleterious effects of the NSAID on the gastroduodenal mucosa, i.e., the acid inhibitor is released first and the release of NSAID is delayed until after the pH in the GI tract has risen. In a preferred embodiment, the unit dosage form is a multilayer tablet, having an outer layer comprising the acid inhibitor and an inner core which comprises the NSAID. In the most preferred form, coordinated delivery is accomplished by having the inner core surrounded by a polymeric barrier coating that does not dissolve unless the surrounding medium is at a pH of at least 3.5, preferably at least 4 and more preferably, at least 5. Alternatively, a barrier coating may be employed which controls the release of NSAID by time, as opposed to pH, with the rate adjusted so that NSAID is not released until after the pH of the gastrointestinal tract has risen to at least 3.5, preferably at least 4, and more preferably at least 5. Thus, a time-release formulation may be used to prevent the gastric presence of NSAID until mucosal tissue is no longer exposed to the damage enhancing effect of very low pH.

The invention includes methods of treating a patient for pain, inflammation and/or other conditions by administering the pharmaceutical compositions described above. Although the method may be used for any condition in which an NSAID is effective, it is expected that it will be particularly useful in patients with osteoarthritis or rheumatoid arthritis. Other conditions that may be treated include, but are not limited to: all form of headache, including migraine headache; acute musculoskeletal pain; ankylosing spondylitis; dysmenorrhoea; myalgias; and neuralgias.

In a more general sense, the invention includes methods of treating pain, inflammation and/or other conditions by orally administering an acid inhibitor at a dose effective to raise a patient's gastric pH to at least 3.5, preferably to at least 4 or and more preferably to at least 5. The patient is also administered an NSAID, for example in a coordinated dosage form, that has been coated in a polymer that only dissolves at a pH of least 3.5, preferably at least 4 and, more preferably, 5 or greater or which dissolves at a rate that is slow enough to prevent NSAID release until after the pH has been raised. When acid inhibitor and NSAID are administered in separate doses, e.g., in two separate tablets, they should be given concomitantly (i.e., so that their biological effects overlap) and may be given concurrently, i.e., NSAID is given within one hour after the acid inhibitor. Preferably, the acid inhibitor is an H2 blocker and, in the most preferred embodiment, it is famotidine at a dosage of between 5 mg and 100 mg. Any of the NSAIDs described above may be used in the method but naproxen at a dosage of between 200 and 600 mg is most preferred. It is expected that the inhibitor and analgesic will be typically delivered as part of a single unit dosage form which provides for the coordinated release of therapeutic agents. The most preferred dosage form is a multilayer tablet having an outer layer comprising an H2 blocker and an inner core comprising an NSAID.

The invention also provides a method for increasing compliance in a patient requiring frequent daily dosing of NSAIDs by providing both an acid inhibitor and NSAID in a single convenient, preferably coordinated, unit dosage form, thereby reducing the number of individual doses to be administered during any given period.

DETAILED DESCRIPTION OF THE INVENTION

The present invention is based upon the discovery of improved pharmaceutical compositions for administering NSAIDs to patients. In addition to containing one or more NSAIDs, the compositions include acid inhibitors that are capable of raising the pH of the GI tract of patients. All of the dosage forms are designed for oral delivery and provide for the coordinated release of therapeutic agents, i.e., for the sequential release of acid inhibitor followed by analgesic.

The NSAIDs used in preparations may be either short or long acting. As used herein, the term "long acting" refers to an NSAID having a pharmacokinetic half-life of at least 2 hours, preferably at least 4 hours and more preferably, at least 8–14 hours. In general, its duration of action will equal or exceed about 6–8 hours. Examples of long-acting NSAIDs are: flurbiprofen with a half-life of about 6 hours; ketoprofen with a half-life of about 2 to 4 hours; naproxen or naproxen sodium with half-lives of about 12 to 15 hours and about 12 to 13 hours respectively; oxaprozin with a half life of about 42 to 50 hours; etodolac with a half-life of about 7 hours; indomethacin with a half life of about 4 to 6 hours; ketorolac with a half-life of up to about 8–9 hours, nabumetone with a half-life of about 22 to 30 hours; mefenamic acid with a half-life of up to about 4 hours; and piroxicam with a half-life of about 4 to 6 hours. If an NSAID does not naturally have a half-life sufficient to be long acting, it can, if desired, be made long acting by the way in which it is formulated. For example, NSAIDs such as acetaminophen and aspirin may be formulated in a manner to increase their half-life or duration of action. Methods for making appropriate formulations are well known in the art (see e.g. *Remington's Pharmaceutical Sciences*, 16th ed., A. Oslo editor, Easton, Pa. (1980)).

It is expected that a skilled pharmacologist may adjust the amount of drug in a pharmaceutical composition or administered to a patient based upon standard techniques well known in the art. Nevertheless, the following general guidelines are provided:

Indomethacin is particularly useful when contained in tablets or capsules in an amount from about 25 to 75 mg. A typical daily oral dosage of indomethacin is three 25 mg doses taken at intervals during the day. However, daily dosages of up to about 150 mg are useful in some patients.

Aspirin will typically be present in tablets or capsules in an amount of between about 250 mg and 1000 mg. Typical daily dosages will be in an amount ranging from 500 mg to about 10 g.

Ibuprofen may be provided in tablets or capsules of 50, 100, 200, 300, 400, 600, or 800 mg. Daily doses should not exceed 3200 mg. 200 mg-800 mg may be particularly useful when given 3 or 4 times daily.

Flurbiprofen is useful when in tablets at about from 50 to 100 mg. Daily doses of about 100 to 500 mg, and particularly from about 200 to 300 mg, are usually effective.

Ketoprofen is useful when contained in tablets or capsules in an amount of about 25 to 75 mg. Daily doses of from 100 to 500 mg and particularly of about 100 to 300 mg are typical as is about 25 to 50 mg every six to eight hours.

Naproxen is particularly useful when contained in tablets or capsules in an amount of from 250 to 500 mg. For naproxen sodium, tablets of about 275 or about 550 mg are typically used. Initial doses of from 100 to 1250 mg, and particularly 350 to 800 mg are also used, with doses of about 550 mg being generally preferred.

Oxaprozin may be used in tablets or capsules in the range of roughly 200 mg to 1200 mg, with about 600 mg being preferred. Daily doses of 1200 mg have been found to be particularly useful and daily doses should not exceed 1800 mg or 26 mg/kg.

Etodolac is useful when provided in capsules of 200 mg to 300 mg or in tablets of about 400 mg. Useful doses for acute pain are 200–400 mg every six-eight hours, not to exceed 1200 mg/day. Patients weighing less than 60 kg are advised not to exceed doses of 20 mg/kg. Doses for other uses are also limited to 1200 mg/day in divided doses, particularly 2, 3 or 4 times daily.

Ketorolac is usefully provided in tablets of 1–50 mg, with about 10 mg being typical. Oral doses of up to 40 mg, and particularly 10–30 mg/day have been useful in the alleviation of pain.

Nabumetone may be provided in tablets or capsules of between 500 mg and 750 mg. Daily doses of 1500–2000 mg, after an initial dose of 100 mg, are of particular use.

Mefenamic acid is particularly useful when contained in tablets or capsules of 50 mg to 500 mg, with 250 mg being typical. For acute pain, an initial dosage of 1–1000 mg, and particularly about 500 mg, is useful, although other doses may be required for certain patients.

Lomoxicam is provided in tablets of 4 mg or 8 mg. Useful doses for acute pain are 8 mg or 16 mg daily, and for arthritis are 12 mg daily.

One particular group of long acting NSAIDs that may be used are the cyclooxygenase-2 inhibitors. These include: celecoxib, rofecoxib, meloxicam, piroxicam, valdecoxib, parecoxib, etoricoxib, CS-502, JTE-522, L-745,337, or NS398. JTE-522, L-745,337 and NS398 as described, inter alia, in Wakatani, et al. (*Jpn. J. Pharmacol.* 78:365–371 (1998)) and Panara, et al. (*Br. J. Pharmacol.* 116:2429–2434 (1995)). The amount present in a tablet or administered to a patient will depend upon the particular COX-2 inhibitor being used. For example:

Celecoxib may be administered in a tablet or capsule containing from about 100 mg to about 500 mg or, preferably, from about 100 mg to about 200 mg.

Piroxicam may be used in tablets or capsules containing from about 10 to 20 mg.

Rofecoxib will typically be provided in tablets or capsules in an amount of 12.5, 25 or 50 mg. The recommended initial daily dosage for the management of acute pain is 50 mg.

Meloxicam is provided in tablets of 7.5 mg, with a recommended daily dose of 7.5 or 15 mg for the management of osteoarthritis.

Valdecoxib is provided in tablets of 10 or 20 mg, with a recommended daily dose of 10 mg for arthritis or 40 mg for dysmenorrhea.

With respect to acid inhibitors, tablets or capsules may contain anywhere from 1 mg to as much as 1 g. Typical amounts for H2 blockers are: cimetidine, 100 to 800 mg/unit dose; ranitidine, 50–300 mg/unit dose; famotidine, 5–100 mg/unit dose; ebrotidine 400–800 mg/unit dose; pabutidine 40 mg/unit dose; lafutidine 5–20 mg/unit dose; and nizatidine, 50–600 mg/unit dose. Proton pump inhibitors will typically be present at about 5 mg to 600 mg per unit dose. For example, the proton pump inhibitor omeprazole should be present in tablets or capsules in an amount from 5 to 50 mg, with about 20 mg per unit dosage form being preferred. Other typical amounts are: esomeprazole, 5–100 mg, with about 40 mg per unit dosage form being preferred; lansoprazole, 15–150 mg, with about 30 mg per unit dosage form being preferred; pantoprazole, 10–200 mg, with about 40 mg per unit dosage form being preferred; and rabeprazole, 5–100 mg, with about 20 mg per unit dosage form being preferred.

Making of Pharmaceutical Preparations

The pharmaceutical compositions of the invention include tablets, dragees, liquids and capsules and can be made in accordance with methods that are standard in the art (see, e.g., *Remington's Pharmaceutical Sciences*, 16$^{th}$ ed., A Oslo editor, Easton, Pa. (1980)). Drugs and drug combinations will typically be prepared in admixture with conventional excipients. Suitable carriers include, but are not limited to: water; salt solutions; alcohols; gum arabic; vegetable oils; benzyl alcohols; polyethylene glycols; gelatin; carbohydrates such as lactose, amylose or starch; magnesium stearate; talc; silicic acid; paraffin; perfume oil; fatty acid esters; hydroxymethylcellulose; polyvinyl pyrrolidone; etc. The pharmaceutical preparations can be sterilized and, if desired, mixed with auxiliary agents such as: lubricants, preservatives, disintegrants; stabilizers; wetting agents; emulsifiers; salts; buffers; coloring agents; flavoring agents; or aromatic substances.

Enteric coating layer(s) may be applied onto the core or onto the barrier layer of the core using standard coating techniques. The enteric coating materials may be dissolved or dispersed in organic or aqueous solvents and may include one or more of the following materials: methacrylic acid copolymers, shellac, hydroxypropylmethcellulose phthalate, polyvinyl acetate phthalate, hydroxypropylmethylcellulose trimellitate, carboxymethylethylcellulose, cellulose acetate phthalate or other suitable enteric coating polymer(s). The pH at which the enteric coat will dissolve can be controlled by the polymer or combination of polymers selected and/or ratio of pendant groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included.

The Making of Tablet Dosage Forms

Preferably, the combination of an acid inhibitor and an NSAID will be in the form of a bi- or multi-layer tablet. In a bilayer configuration, one portion of the tablet contains the acid inhibitor in the required dose along with appropriate excipients, agents to aid dissolution, lubricants, fillers, etc. The second portion of the tablet will contain the NSAID, preferably naproxen, in the required dose along with other excipients, dissolution agents, lubricants, fillers, etc. In the most preferred embodiment, the NSAID layer is surrounded by a polymeric coating which does not dissolve at a pH of less than 4. The naproxen may be granulated by methods such as slugging, low- or high-shear granulation, wet granulation, or fluidized-bed granulation. Of these processes, slugging generally produces tablets of less hardness and greater friability. Low-shear granulation, high-shear granulation, wet granulation and fluidized-bed granulation generally produce harder, less friable tablets.

EXAMPLES

Example 1

Enteric Coated Naproxen Sodium Core and Famotidine Immediate Release

Figure 1:
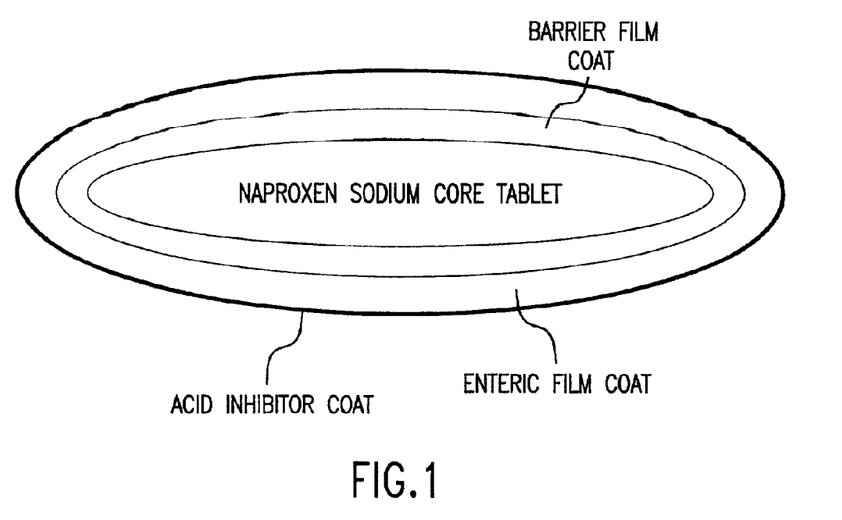
FIG. 1 is a schematic diagram of a four layer tablet dosage form. There is a naproxen core layer surrounded by a barrier layer. A third, enteric coating, layer delays the release of naproxen sodium until the pH is at a specific level, e.g., above 4. Finally, there is an outer layer that releases an acid inhibitor such as famotidine.

A schematic diagram of a four layer tablet dosage form is shown in FIG. 1. The first layer contains naproxen sodium distributed throughout a matrix of pharmaceutically acceptable fillers, excipients, binding agents, disintegrants, and lubricants.

The second layer is a barrier layer which protects the first layer containing naproxen sodium. The barrier film coat is applied by conventional pan coating technology and the weight of the barrier coat may vary from 1% to 3% of the core tablet weight. In particular embodiments, the core naproxen sodium tablet is coated with coating ingredients such as Opaspray® K-1-4210A or Opadry® YS-1-7006 (Colorcon, West Point, Pa.). Polymer film coating ingredients such as hydroxypropylmethylcellulose 2910 and polyethylene glycol 8000 in a coating suspension may also be used.

The function of the third layer is to prevent the release of naproxen sodium until the dosage form reaches an environment where the pH is above about 4 or 5. The enteric coating does not dissolve in areas of the GI tract where the pH may be below about 4 or 5 such as in an unprotected stomach. Methacrylic acid copolymers are used as the enteric coating ingredient, triethyl citrate and dibutyl phthalate are plasticisers, and ammonium hydroxide is used to adjust the pH of the dispersion. The coating dissolves only when the local pH is above, for example, 5.5 and, as a result, naproxen sodium is released.

The outermost layer contains an "acid inhibitor" in an effective amount which is released from the dosage form immediately after administration to the patient. The acid inhibitor in the present example is a proton pump inhibitor or, preferably the H2 blocker famotidine, which raises the pH of the gastrointestinal tract to above 4. The typical effective amount of famotidine in the dosage form will vary from 5 mg to 100 mg. A typical film coating formulation contains Opadry Clear® YS-1-7006 which helps in the formation of the film and in uniformly distributing famotidine within the fourth layer without tablets sticking to the coating pan or to each other during application of the film coat. Other ingredients may include: plasticisers such as triethyl citrate, dibutyl phthalate, and polyethylene glycol; anti-adhering agents such as talc; lubricating ingredients such as magnesium stearate; and opacifiers such as titanium dioxide. In addition, the pH of the film coating solution can be adjusted to aid in dissolution of the famotidine. The film coating is thin and rapidly releases famotidine for absorption.

|                                                    | % W/W   | mg/Tablet |
|----------------------------------------------------|---------|-----------|
| Core Tablet Ingredients                            |         |           |
| Naproxen sodium, USP                               | 74.074  | 500.00    |
| Microcrystalline cellulose, NF (Avicel PH 200)     | 17.166  | 115.87    |
| Povidone (K29/32), USP                             | 3.450   | 23.29     |
| Talc, USP                                          | 4.350   | 29.36     |
| Magnesium Stearate, NF                             | 0.960   | 6.48      |
| Total                                              | 100.00  | 675.00    |
| Barrier Film Coating Ingredients                   |         |           |
| Opadry Clear ® YS-1-7006                           | 5.00    |           |
| Purified water USP                                 | 95.00   |           |
| Total                                              | 100.00  |           |
| Enteric Coating Dispersion Ingredients             |         |           |
| Methacrylic Acid Copolymer, NF (Eudragit L-100-55) | 7.30    |           |
| Methacrylic Acid Copolymer, NF (Eudragit L-100)    | 7.30    |           |
| Triethyl Citrate, NF                               | 2.95    |           |
| Dibutyl Phthalate, NF                              | 1.17    |           |
| Ammonium Hydroxide (30%), NF                       | 0.87    |           |
| Purified water, USP                                | 80.41   |           |
| Total                                              | 100.00  |           |
| Famotidine Coating Dispersion Ingredients          |         |           |
| Famotidine, USP                                    | 3.0     |           |
| Opadry Clear ® (YS-1-7006)                         | 5.0     |           |
| Talc, USP                                          | 3.0     |           |
| Purified Water, USP                                | 89.0    |           |
| Total                                              | 100.0   |           |

Example 2

Enteric Coated Naproxen Core and Famotidine Immediate Release

Figure 2:
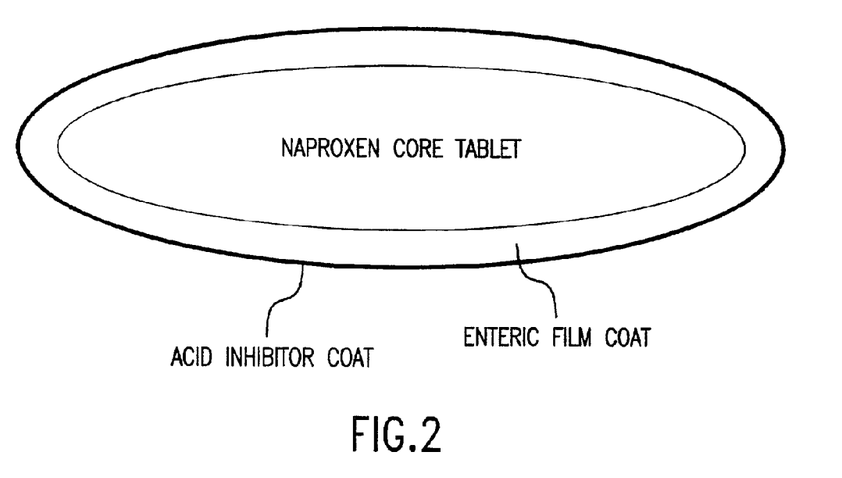
FIG. 2 illustrates a three layer dosage form. An acid inhibitor, e.g., famotidine, is released immediately after ingestion by a patient in order to raise the pH of the gastrointestinal tract to above a specific pH, e.g., above 4. The innermost layer contains naproxen. Thus, the dosage form has a naproxen core, an enteric film coat and an acid inhibitor film coat.

FIG. 2 illustrates a three layered dosage form which releases famotidine immediately after ingestion by the patient in order to raise the pH of the gastrointestinal tract to above about 4. The innermost layer contains naproxen uniformly distributed throughout a matrix of pharmaceutically acceptable excipients. These excipients perform specific functions and may serve as binders, disintegrants, or lubricants. A pharmaceutically acceptable enteric coating surrounds the naproxen core. The function of the enteric coat is to delay the release of naproxen until the dosage form reaches an environment where the pH is above about 4. The coating does not dissolve in the harshly acidic pH of the unprotected stomach. It contains methacrylic acid copolymers which prevent the release of naproxen in the unprotected stomach. Also included are: triethyl citrate, a plasticiser; simethicone emulsion, an anti-foaming agent; and sodium hydroxide which is used to adjust the pH of the dispersion.

The outermost layer contains an "acid inhibitor" in an effective amount which is released from the dosage form immediately after administration to the patient. The acid inhibitor in this example is a proton pump inhibitor or, preferably, the H2 blocker famotidine which raises the pH of the stomach to above 4. A typical film coating formulation contains Opadry Clear® YS-1-7006 which helps in the formation of the film and in uniformly distributing famotidine in the fourth layer without tablets sticking to the coating pan or sticking to each other during application of the film coat. Other ingredients are: plasticisers such as polyethylene glycol 8000; anti-adhering agents such as talc; lubricating ingredients such as magnesium stearate;, and opacifiers such as titanium dioxide. In addition, the pH of the film coating solution can be adjusted to aid in dissolution of the famotidine. The film coating is thin and rapidly releases famotidine for absorption.

|                                                     | % W/W  | mg/Tablet |
|-----------------------------------------------------|--------|-----------|
| Core Tablet Ingredients                             |        |           |
| Naproxen, USP                                       | 90.91  | 500.00    |
| Povidone K-90, USP                                  | 2.00   | 11.00     |
| Starch, USP                                         | 2.59   | 14.25     |
| Croscarmellose Sodium, USP                          | 4.00   | 22.00     |
| Magnesium Stearate, NF                              | 0.50   | 2.75      |
| Total                                               | 100.00 | 550.00    |
| Purified Water, USP qs                              |        |           |
| Enteric Coating Dispersion Ingredients              |        |           |
| Methacrylic Acid Copolymer Type C, NF (Eudragit L-100-55) | 14.5 |           |
| Talc, USP                                           | 3.8    |           |
| Sodium Hydroxide, NF                                | 0.2    |           |
| Triethyl Citrate, NF                                | 1.7    |           |
| Simethicone Emulsion, USP                           | 0.02   |           |
| Purified Water, USP                                 | 79.78  |           |
| Total                                               | 100.00 |           |
| Famotidine Coating Dispersion Ingredients           |        |           |
| Famotidine, USP                                     | 3.0    |           |
| Opadry Clear ® (YS-1-7006)                          | 5.0    |           |
| Talc, USP                                           | 3.0    |           |
| Purified Water, USP                                 | 89.0   |           |
| Total                                               | 100.0  |           |

Example 3

Naproxen Controlled Release Core and Famotidine Immediate Release

A trilayer tablet which separates famotidine contained in the film coat from controlled-release naproxen may be used in the present invention. The core tablet of naproxen is formulated using excipients which control the drug release for therapeutic relief from pain and inflammation for 24 hours. FIG. 2 shows an example of an appropriate trilayer tablet. In this particular example, naproxen is mixed with a polymeric material, hydroxypropylmethylcellulose and granulated with water. The granules are dried, milled, and blended with a lubricant, such as magnesium stearate. They are then compacted into tablets.

The controlled-release core tablet of naproxen is film coated with a pharmaceutically acceptable enteric coating. The function of the enteric coat is to delay the release of naproxen until the dosage form reaches an environment where the pH is above about 4. The coating does not dissolve in the extremely acidic pH of the unprotected stomach. The function of methacrylic acid copolymers is to prevent the release of naproxen until the pH of the stomach rises. Triethyl citrate is a plasticiser, simethicone emulsion is a anti-foaming agent, and sodium hydroxide is used to adjust the pH of the dispersion.

The outermost layer contains an "acid inhibitor" which is released from the dosage form immediately after administration to the patient. The acid inhibitor in the present example is a proton pump inhibitor or, preferably, the H2 blocker famotidine which consistently raises the pH of the stomach to above 4. The typical effective amount of famotidine in the dosage will vary from 5 mg to 100 mg. A typical film coating formulation contains Opadry Blue® YS-1-4215 which is essential for film formation and for the uniform application of famotidine to the core tablet. Polymer film coating ingredients, hydroxypropylmethylcellulose or Opaspray® K-1-4210A (Colorcon, West Point, Pa.) may also be used. Other ingredients which help in the formation of the film and in the uniform application of famotidine to the core tablet are: plasticisers such as triethyl citrate and dibutyl phthalate; anti-adhering agents such as talc; lubricating ingredients such as magnesium stearate; and opacifiers such as titanium dioxide. In addition, the pH of the film coating solution can be adjusted to aid in dissolution of the famotidine. The film coating is thin and rapidly releases famotidine for absorption.

|  | % W/W | mg/Tablet |
|---|---|---|
| Core Tablet Ingredients |  |  |
| Naproxen, USP | 94.00 | 750 |
| Hydroxypropyl methylcellulose 2208, USP (viscosity 15000 cps) | 5.00 | 39.9 |
| Magnesium Stearate, NF | 1.00 | 7.95 |
| Total | 100.00 | 797.85 |
| Enteric Coating Dispersion Ingredients |  |  |
| Methacrylic Acid Copolymer Type C, NF (Eudragit L-100-55) | 14.5 |  |
| Talc, USP | 3.8 |  |
| Sodium Hydroxide, NF | 0.2 |  |
| Triethyl Citrate, NF | 1.7 |  |
| Simethicone Emulsion, USP | 0.02 |  |
| Purified Water, USP | 79.78 |  |
| Total | 100.00 |  |
| Famotidine Coating Dispersion Ingredients |  |  |
| Famotidine, USP | 2.0 |  |
| Opadry Blue ® (YS-1-4215) | 10.0 |  |
| Talc, USP | 9.0 |  |
| Purified Water, USP | 79.0 |  |
| Total | 100.0 |  |

Example 4

Naproxen and Famotidine Controlled Release Core and Famotidine Immediate Release A trilayer tablet which separates famotidine contained in the film coat from controlled-release naproxen and famotidine may be used in the present invention. The core tablet of naproxen and famotidine is formulated using excipients which control the drug release for therapeutic relief from pain and inflammation for 24 hours. FIG. 2 is an example of an appropriate trilayer tablet. In this particular example, naproxen and famotidine are mixed with a polymeric material, hydroxypropylmethylcellulose and granulated with water. The granules are dried, milled, and blended with a lubricant, such as magnesium stearate. They are then compacted into tablets.

The controlled-release core tablet of naproxen and famotidine is film coated with a pharmaceutically acceptable enteric coating. The function of the enteric coat is to delay the release of naproxen until the dosage form reaches an environment where the pH is above about 4. The coating does not dissolve in the extremely acidic pH of the unprotected stomach. The function of methacrylic acid copolymers is to prevent the release of naproxen in the pH of the stomach rises. Triethyl citrate is a plasticiser, simethicone emulsion is a anti-foaming agent, and sodium hydroxide is used to adjust the pH of the dispersion.

The outermost later contains an "acid inhibitor" which is released from the dosage form immediately after administration to the patient. The acid inhibitor in the present example is a proton pump inhibitor or, preferably, the H2 blocker famotidine which consistently raises the pH of the stomach to above 4. The typical effective amount of famotidine in the dosage will vary from 5 mg to 100 mg. A typical film coating formulation contains Opadry Blue® YS-1-4215 which is essential for film formation and for the uniform application of famotidine to the core tablet. Polymer film coating ingredients, hydroxypropylmethylcellulose or Opaspray® K-1-4210A (Colorcon, West Point, Pa.) may also be used. Other ingredients which help in the formation of the film and in the uniform application of famotidine to the core tablet are: plasticisers such as triethyl citrate and dibutyl phthalate; anti-adhering agents such as talc; lubricating ingredients such as magnesium stearate; and opacifiers such as titanium dioxide. In addition, the pH of the film coating solution can be adjusted to aid in dissolution of the famotidine. The film coating is thin and rapidly releases famotidine for absorption.

|  | % W/W | mg/Tablet |
|---|---|---|
| Core Tablet Ingredients |  |  |
| Naproxen, USP | 88.05 | 500 |
| Famotidine, USP | 3.52 | 20.0 |
| Hydroxypropyl methylcellulose 2208, USP (viscosity 15000 cps) | 7.03 | 39.9 |
| Magnesium Stearate, NF | 1.40 | 7.95 |
| Total | 100.00 | 567.85 |
| Enteric Coating Dispersion Ingredients |  |  |
| Methacrylic Acid Copolymer Type C, NF (Eudragit L-100-55) | 14.5 |  |
| Talc, USP | 3.8 |  |
| Sodium Hydroxide, NF | 0.2 |  |
| Triethyl Citrate, NF | 1.7 |  |
| Simethicone Emulsion, USP | 0.02 |  |
| Purified Water, USP | 79.78 |  |
| Total | 100.00 |  |
| Famotidine Coating Dispersion Ingredients |  |  |
| Famotidine, USP | 2.0 |  |
| Opadry Blue ® (YS-1-4215) | 10.0 |  |
| Talc, USP | 9.0 |  |
| Purified Water, USP | 79.0 |  |
| Total | 100.0 |  |

Example 5

Enteric Coated Naproxen Sodium Core and Pantoprazole Immediate Release in Film Coat A schematic diagram of a four layer tablet dosage form is shown in FIG. 1. The first layer contains naproxen sodium distributed throughout a matrix of pharmaceutically acceptable fillers, excipients, binding agents, disintegrants, and lubricants.

The second layer is a barrier layer which protects the first layer containing naproxen sodium. The barrier film coat is applied by conventional pan coating technology and the weight of the barrier coat may vary from 1% to 3% of the core tablet weight. In particular embodiments, the core naproxen sodium tablet is coated with coating ingredients such as Opaspray® K-1-4210A or Opadry® YS-1-7006 (Colorcon, West Point, Pa.). Polymer film coating ingredients such as hydroxypropylmethylcellulose 2910 and polyethylene glycol 8000 in a coating suspension may also be used.

The third layer is an enteric film coat. It does not dissolve in areas of the GI tract where the pH may be below 4 such as in an unprotected stomach but it dissolves only when the local pH is above about 4. Therefore, the function of the third layer is to prevent the release of naproxen sodium until the dosage form reaches an environment where the pH is above 4. In this example, hydroxypropylmethylcellulose phthalate is the enteric coating ingredient, cetyl alcohol is a plasticiser and acetone and alcohol are solvents.

The fourth layer contains an "acid inhibitor" in an effective amount which is released from the dosage form as soon as the film coat dissolves. The acid inhibitor in this example is a proton pump inhibitor, pantoprazole which raises the pH of the gastrointestinal tract to above 4. The typical effective amount of pantoprazole in the dosage form may vary from 10 mg to 200 mg. The film coat is applied by conventional pan coating technology and the weight of film coat may vary from 4% to 8% of the core tablet weight. Other ingredients are, plasticisers such as triethyl citrate, dibutyl phthalate, anti-adhering agents such as talc, lubricating ingredients such as magnesium stearate, opacifiers such as, titanium dioxide, and ammonium hydroxide to adjust the pH of the dispersion. The film coating is thin and rapidly releases pantoprazole for absorption. Therefore, pantoprazole releases first and then the core erodes and releases naproxen sodium.

| Core Tablet Ingredients | % W/W | mg/tablet |
| --- | --- | --- |
| Naproxen sodium, USP | 74.075 | 500.00 |
| Microcrystalline cellulose, NF (Avicel PH 200) | 17.165 | 115.87 |
| Povidone (K29/32), USP | 3.450 | 23.29 |
| Talc, USP | 4.350 | 29.36 |
| Magnesium Stearate, NF | 0.960 | 6.48 |
| Total | 100.00 | 675.00 |

Naproxen sodium, 50% microcrystalline cellulose and povidone are dry mixed and wet granulated in an appropriate granulator with sufficient purified water. The wet granules are dried, milled, and blended with the remaining 50% microcrystalline cellulose, talc and magnesium stearate. The final granule blend is compressed into tablets.

| Barrier Film Coating Ingredients | % W/W |
| --- | --- |
| Opadry ® Clear YS-1-7006 | 5.00 |
| Purified Water, USP | 95.00 |
| Total | 100.00 |

Opadry clear is added slowly to purified water and mixing is continued until Opadry is fully dispersed. The solution is sprayed on to the tablet cores in a conventional coating pan until proper amount of Opadry clear is deposited on the tablets.

| Enteric Coating Ingredients | % W/W |
| --- | --- |
| Hydroxypropyl methylcellulose phthalate, NF | 5.5 |
| Cetyl alcohol, NF | 0.3 |
| Acetone, NF | 66.3 |
| Alcohol, USP | 27.9 |
| Total | 100.00 |

Hydroxypropylmethylcellulose phthalate and cetyl alcohol are dissolved in a mixture of alcohol and acetone. The solution is then sprayed on to the tablet bed in proper coating equipment. A sample of the tablets is tested for gastric resistance and the coating stopped if the tablets pass the test.

| Pantoprazole Film Coating Ingredients | % W/W |
| --- | --- |
| Pantoprazole sodium, USP | 5.00 |
| Opadry ® Clear YS-1-7006 | 5.00 |
| Sodium carbonate, NF | 1.20 |
| Purified Water, USP | 88.80 |
| Total | 100.00 |

Pantoprazole sodium is dissolved in purified water containing sodium carbonate in solution. After thorough mixing, Opadry clear is added slowly and mixing is continued until Opadry is fully dispersed. The suspension is sprayed on to the tablet cores in a conventional coating pan until the proper amount of pantoprazole sodium is deposited.

Example 6

Enteric Coated Naproxen Sodium Core and Omeprazole Immediate Release in Film Coat A schematic diagram of a four layer tablet dosage form is shown in FIG. 1. The first layer contains naproxen sodium distributed throughout a matrix of pharmaceutically acceptable fillers, excipients, binding agents, disintegrants, and lubricants.

The second layer is a barrier layer which protects the first layer containing naproxen sodium. The barrier film coat is applied by conventional pan coating technology and the weight of the barrier coat may vary from 1% to 3% of the core tablet weight. In particular embodiments, the core naproxen sodium tablet is coated with coating ingredients such as Opaspray® K-1-4210A or Opadry® YS-1-7006 (Colorcon, West Point, Pa.). Polymer film coating ingredients such as hydroxypropylmethylcellulose 2910 and polyethylene glycol 8000 in a coating suspension may also be used.

The third layer is an enteric film coat. It does not dissolve in areas of the GI tract where the pH is below 4 such as in an unprotected stomach but it dissolves only when the local pH is above 4. Therefore, the function of the third layer is to prevent the release of naproxen sodium until the dosage form reaches an environment where the pH is above about 4. In this example, hydroxypropylmethylcellulose phthalate is the enteric coating ingredient, cetyl alcohol is a plasticiser and acetone and alcohol are solvents.

The fourth layer contains an "acid inhibitor" in an effective amount which is released from the dosage form as soon as the film coat dissolves. The acid inhibitor in this example is a proton pump inhibitor, omeprazole, which raises the pH of the gastrointestinal tract to above 4. The typical effective amount of omeprazole in the dosage form may vary from 5 mg to 50 mg. The film coat is applied by conventional pan coating technology and the weight of film coat may vary from 4% to 8% of the core tablet weight. Other ingredients are, plasticisers such as triethyl citrate, dibutyl phthalate, anti-adhering agents such as talc, lubricating ingredients such as magnesium stearate, opacifiers such as, titanium dioxide, and ammonium hydroxide to adjust the pH of the dispersion. The film coating is thin and rapidly releases omeprazole for absorption. Therefore, omeprazole is released first and then the core erodes and releases naproxen sodium.

| Core Tablet Ingredients | % W/W | mg/tablet |
| --- | --- | --- |
| Naproxen sodium, USP | 74.075 | 500.00 |
| Microcrystalline cellulose, NF (Avicel PH 200) | 17.165 | 115.87 |
| Povidone (K29/32), USP | 3.450 | 23.29 |
| Talc, USP | 4.350 | 29.36 |
| Magnesium Stearate, NF | 0.960 | 6.48 |
| Total | 100.00 | 675.00 |

Naproxen sodium, 50% microcrystalline cellulose and povidone are dry mixed and wet granulated in an appropriate granulator with sufficient purified water. The wet granules are dried, milled, and blended with the remaining 50% microcrystalline cellulose, talc and magnesium stearate. The final granule blend is compressed into tablets.

| Barrier Film Coating Ingredients | % W/W |
| --- | --- |
| Opadry ® Clear YS-1-7006 | 5.00 |
| Purified Water, USP | 95.00 |
| Total | 100.00 |

Opadry clear is added slowly to purified water and mixing is continued until Opadry is fully dispersed. The solution is sprayed on to the tablet cores in a conventional coating pan until the proper amount of Opadry clear is deposited on the tablets.

| Enteric Coating Ingredients | % W/W |
| --- | --- |
| Methacrylic Acid Copolymer, NF (Eudragit L-100-55) | 6.0 |
| Triethyl Citrate, NF | 0.6 |
| Talc, USP | 3.0 |
| Purified Water, USP | 5.0 |
| Isopropyl Alcohol, USP | 85.40 |
| Total | 100.00 |

Methacrylic acid copolymer, triethyl citrate, and talc are dissolved in a mixture of isopropyl alcohol and water. The solution is then sprayed on to the tablet bed in a proper coating equipment. A sample of the tablets is tested for gastric resistance and the coating is stopped if the tablets pass the test.

| Omeprazole Film Coating Ingredients | % W/W |
| --- | --- |
| Omeprazole, USP | 5.00 |
| Opadry ® Clear YS-1-7006 | 5.00 |
| Purified Water, USP | 10.00 |
| Isopropyl Alcohol, USP | 80.00 |
| Total | 100.00 |

Omeprazole is dissolved in a purified water and isopropyl alcohol mixture. After thorough mixing, Opadry clear is added slowly and mixing is continued until Opadry is fully dispersed. The suspension is sprayed on to the tablet cores in a conventional coating pan until proper amount of omeprazole is deposited on the tablets.

Example 7

Naproxen Sodium Delayed Release and Omeprazole Immediate Release Capsule

A coordinated delivery dosage may be used to provide fast release of an acid inhibitor, a proton pump inhibitor, omeprazole which raises the pH of the gastrointestinal tract to above 4, and the delayed release of a non-steroidal anti-inflammatory drug, naproxen sodium. Omeprazole granules modify the pH of the stomach such that the drug readily dissolves and is absorbed in the stomach without significant degradation. The typical effective amount of omeprazole in the dosage form may vary from 5 mg to 50 mg. The release of naproxen sodium is delayed by enteric coating.

Omeprazole granules contain an alkalizing excipient such as sodium bicarbonate. Other soluble alkalizing agents such as potassium bicarbonate, sodium carbonate, sodium hydroxide, or their combinations may also be used. The alkalizing agent helps solubilize and protect omeprazole from degradation before its absorption. Sodium lauryl sulfate helps in the wetting of omeprazole. Other surfactants may be used to perform the same function. In the present example, hydroxypropyl methylcellulose helps in granule formation, sodium starch glycolate is a disintegrant, and magnesium stearate is a lubricant. Other excipients may also be used to perform these functions.

Figure 3:
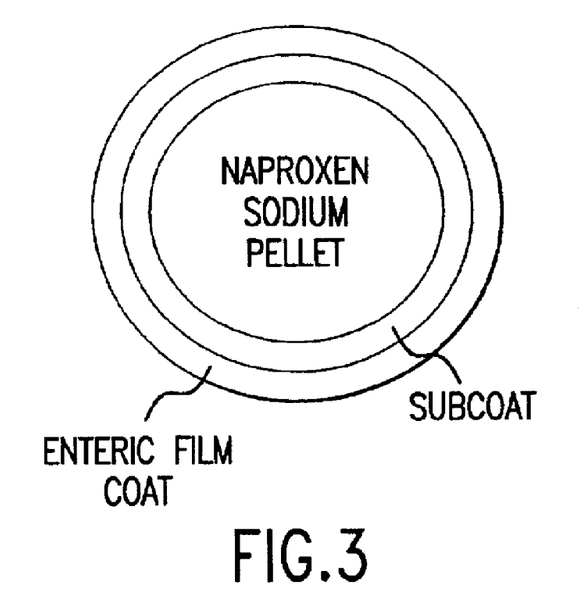
FIG. 3 illustrates a naproxen sodium pellet which contains a subcoat or barrier coat prior to the enteric film coat.

Naproxen sodium pellets as shown in FIG. 3 are prepared by the wet massing technique and the conventional extrusion and spheronization process. The excipients used in the formulation are microcrystalline cellulose, and povidone. The pellets after drying and classification are coated with a protective subcoating containing povidone. Other coating ingredients may also be used such as Opaspray K-1-4210A or Opadry YS-1-7006 (trademarks of Colorcon, West Point, Pa.). Polymer film coating ingredients such as hydroxypropylmethylcellulose 2910 and polyethylene glycol 8000 in a subcoating suspension are also alternatives. Other ingredients are, plasticisers such as triethyl citrate, dibutyl phthalate, anti-adhering agents such as talc, lubricating ingredients such as magnesium stearate, opacifiers such as, titanium dioxide.

The subcoated pellets are enteric coated using enteric coating polymers. In this example, the enteric coating polymer is methacrylic acid copolymer and the plasticizer is dibutyl phthalate which are dissolved in a mixture of acetone and alcohol. The enteric film does not dissolve in the acidic pH but dissolves when the pH in the gut is above about pH 6 and releases naproxen sodium.

| Omeprazole Granules | % W/W | mg/capsule |
|---|---|---|
| Omeprazole, USP | 12.9 | 20.00 |
| Sodium Bicarbonate, USP | 82.40 | 127.72 |
| Hydroxypropyl methylcellulose, USP | 2.00 | 3.10 |
| Sodium lauryl sulfate, NF | 0.20 | 0.31 |
| Sodium starch glycolate, NF | 2.00 | 3.10 |
| Magnesium stearate, NF | 0.50 | 0.77 |
| Total | 100 | 100 |

Hydroxypropylmethylcellulose is dissolved in water, then sodium lauryl sulfate is added and the solution is mixed. Omeprazole, microcrystalline cellulose, and sodium bicarbonate are dry mixed together and granulated with the granulating solution. The granulation is mixed until proper granule formation is reached. The granulation is then dried, milled, and blended with magnesium stearate.

| Pellet Ingredients | % W/W | mg/tablet |
|---|---|---|
| Naproxen sodium, USP | 86.80 | 250.00 |
| Microcrystalline cellulose, NF (Avicel PH 200) | 11.10 | 32.00 |
| Povidone (K90), USP | 2.10 | 6.00 |
| Total | 100.00 | 288.00 |

Povidone is dissolved in water. Naproxen sodium and microcrystalline cellulose are dry mixed and granulated with povidone solution. The wet mass is mixed until proper consistency is reached. The wet mass is then pressed through an extruder and spheronized to form pellets. The pellets are then dried and classified into suitable particle size range.

| Subcoat Ingredients | % W/W |
|---|---|
| Povidone (K29-32), USP | 10.00 |
| Alcohol, USP | 90.00 |
| Total | 100.00 |

The pellet cores are coated using povidone solution by a conventional coating pan method to a weight gain of 1–2%.

| Enteric Coating Ingredients | % W/W |
|---|---|
| Methacrylic Acid Copolymer, NF (Eudragit L-100) | 8.20 |
| Diethyl Phthalate, NF | 1.70 |
| Acetone, NF | 33.30 |
| Isopropyl Alcohol, USP | 56.80 |
| Total | 100.0 |

Eudragit L-100 is dissolved in isopropanol and acetone and diethyl phthalate is dissolved. The solution is sprayed on the pellet cores using proper film coating equipment. A sample of the pellets is tested for gastric resistance before stopping the coating process.

Omeprazole fast release granules and naproxen sodium delayed release pellets are blended together and filled into appropriate size capsules to contain 250 mg naproxen sodium and 20 mg omeprazole per capsule.

Example 8

Naproxen Delayed Release and Omeprazole Immediate Release Capsule

The present Example is directed to a coordinated delivery dosage form containing omeprazole and naproxen. The formulation contains 10 mg omeprazole and uses methylcellulose as a binder and croscarmellose sodium as a disintegrant. Naproxen pellets as shown in FIG. 3 do not need a subcoating layer and are enteric coated with an aqueous dispersion of methacrylic acid copolymer. Optionally, these pellets could be compressed into a core and film coated with an acid inhibitor and thereby form a bilayer tablet.

| Omeprazole Granules | % W/W | mg/capsule |
|---|---|---|
| Omeprazole, USP | 6.45 | 10.00 |
| Sodium Bicarbonate, USP | 88.85 | 137.71 |
| Methylcellulose, USP | 2.00 | 3.10 |
| Sodium lauryl sulfate, NF | 0.20 | 0.31 |
| Croscarmellose sodium, NF | 2.00 | 3.10 |
| Magnesium stearate, NF | 0.50 | 0.78 |
| Total | 100 | 100 |

Methylcellulose is dissolved in water, then sodium lauryl sulfate is added to the solution and mixed. Omeprazole, microcrystalline cellulose, and sodium bicarbonate are dry mixed together and granulated with the granulating solution. The granulation is mixed until proper granule formation is reached. The granulation is then dried, milled, and blended with magnesium stearate.

| Pellet Ingredients | % W/W | mg/tablet |
|---|---|---|
| Naproxen, USP | 76.22 | 250.00 |
| Microcrystalline cellulose, NF (Avicel PH 200) | 21.78 | 71.44 |
| Povidone (K90), USP | 2.00 | 6.56 |
| Total | 100.00 | 328.00 |

Povidone is dissolved in water. Naproxen and microcrystalline cellulose are dry mixed and granulated with povidone solution. The wet mass is mixed until proper consistency is reached. The wet mass is then pressed through an extruder and spheronized to form pellets. The pellets are then dried and classified into a suitable particle size range.

| Enteric Coating Ingredients | % W/W |
|---|---|
| Methacrylic Acid Copolymer, NF (Eudragit L30D 30% dispersion) | 15.60 |
| Talc, USP | 7.60 |
| Triethyl citrate, NF | 1.60 |
| Simethicone Emulsion, USP (Silicone antifoam emulsion SE 2) | 0.20 |
| Purified Water, USP | 74.80 |

Eudragit 30D is dispersed in purified water and simethicone emulsion. Talc and triethyl citrate are then dispersed. The suspension is sprayed on the pellet cores using proper film coating equipment. A sample of the pellets is tested for gastric resistance before stopping the coating process. Omeprazole fast release granules and naproxen sodium delayed release pellets are blended together and filled into appropriate size capsules to contain 250 mg naproxen and 10 mg omeprazole per capsule.

Example 9

Clinical Study of the Relationship of Gastric pH to NSAID-induced Gastric Ulcers Sixty-two subjects were enrolled in a clinical study and randomly assigned to three groups. The following three groups were administered study medication twice daily for five days: (a) 550 mg naproxen sodium (n=10), (b) 40 mg famotidine given with 550 mg of naproxen or famotidine followed 90 minutes later by 550 mg naproxen, (n=39) or (c) 20 mg omeprazole followed by 550 mg naproxen sodium (n=13). Gastric pH was measured hourly beginning at the time of dosing of the final daily dose of study medication and for 8–10 hours thereafter. Subjects had a gastric endoscopy performed at the beginning and on Day 5 prior to the morning dose of study medication to identify gastric and duodenal irritation; no subjects were admitted to the study if gastric irritation was present at the time of initial endoscopy.

Five patients, three (33%) in the naproxen alone group and two (5%) in the famotidine/naproxen group, presented with gastroduodenal ulcers at the end of the study. In the naproxen alone group, the pH was greater than 4 only 4% of the time, and in the famotidine/naproxen group the pH was greater than 4 forty-nine percent of the time during the 8–10 hours following naproxen sodium dosing. Additionally, Lanza grade 3 or 4 damage was present in 28% (n=11) of the subjects receiving famotidine/naproxen sodium, and present 100% (n=10) in the naproxen sodium treatment group. Monitoring of gastric acidity on day 5 indicated that patients with Lanza scores of greater than 2 had integrated gastric acidity of greater than 100 mmol-hr./L. Only 20–40% of patients with integrated gastric acidity of less than 100 mmol-hr/L had gastric pathology, whereas all patients with integrated gastric acidity greater than 100 mmol-hr/L had pathology.

Example 10

Famotidine and Enteric Coated Naproxen Reduce Gastroduodenal Damage Due to NSAID Therapy Forty patients are randomized to two groups for a one week study of twice-daily dosing of: 500 mg enteric coated naproxen, and 500 mg enteric coated naproxen preceded by 40 mg famotidine. Endoscopies are conducted on all patients prior to first dosing and on the final day of the study. No subjects have any evidence of gastroduodenal damage at the beginning of the study (at first endoscopy).

At the second endoscopy, Lanza scores for gastroduodenal damage are assessed for all subjects. Subjects in the enteric coated naproxen 500 mg group have a lower incidence of grade 3–4 gastroduodenal damage than subjects previously treated with non-enteric coated naproxen 500 mg. Importantly, subjects administered 500 mg enteric coated naproxen and 40 mg famotidine have substantially lower incidence of grade 3–4 gastroduodenal damage than subjects who had previously taken naproxen alone (either naked or enteric coated) which demonstrates the need for and the value of combining acid inhibition with enteric coating to minimize the gastrointestinal damage of NSAID.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A pharmaceutical composition in unit dose form suitable for oral administration to a patient, comprising:

(a) an acid inhibitor present in an amount effective to raise the gastric pH of said patient to at least 3.5 upon the administration of one or more of said unit dosage forms;

(b) a non-steroidal anti-inflammatory drug (NSAID) in an amount effective to reduce or eliminate pain or inflammation in said patient upon administration of one or more of said unit dosage forms;

and wherein said unit dosage form provides for coordinated release such that:

i) said NSAID is surrounded by a coating that, upon ingestion of said unit dosage form by said patient, prevents the release of essentially any NSAID from said dosage form unless the pH of the surrounding medium is 3.5 or higher;

ii) at least a portion of said acid inhibitor is not surrounded by an enteric coating and, upon ingestion of said unit dosage form by said patient, is released regardless of whether the pH of the surrounding medium is below 3.5 or above 3.5.

2. The pharmaceutical composition of claim 1, wherein said acid inhibitor is an H2 blocker.

3. The pharmaceutical composition of claim 2, wherein said H2 blocker is selected from the group consisting of: cimetidine; ranitidine; ebrotidine; pabutidine; lafutidine; loxtidine and famotidine.

4. The pharmaceutical composition of claim 3, wherein said H2 blocker is famotidine, present in said unit dosage form in an amount of between 5 mg and 100 mg.

5. The pharmaceutical composition of claim 1, wherein said acid inhibitor is a proton pump inhibitor selected from the group consisting of: omeprazole, esomeprazole, lansoprazole, pantoprazole and rabeprazole.

6. The pharmaceutical composition of claim 5, wherein said proton pump inhibitor is pantoprazole, present in said unit dosage form in an amount of between 10 mg and 200 mg.

7. The pharmaceutical composition of claim 1, wherein said NSAID is a cyclooxygenese-2 (COX-2) inhibitor.

8. The pharmaceutical composition of claim 7, wherein said COX-2 inhibitor is selected from the group consisting of celecoxib; rofecoxib; meloxicam; piroxicam; valdecoxib, parecoxib, etoricoxib, CS-502, JTE-522; L-745,337; and NS398.

9. The pharmaceutical composition of claim 1, wherein said NSAID is selected from the group consisting of: aspirin; acetaminophen; ibuprofen; flurbiprofen; ketoprofen; lornoxicam; naproxen; oxaprozin; etodolac; indomethacin; ketorolac; and nabumetone.

10. The pharmaceutical composition of claim 9, wherein said NSAID is naproxen present in an amount of between 50 mg and 1500 mg.

11. The pharmaceutical composition of claim 10, wherein said naproxen is present in an amount of between 200 mg and 600 mg.

12. The pharmaceutical composition of claim 1 wherein said unit dosage form is a multilayer tablet comprising a single core and one or more layers outside of said single core, wherein:
  i) said NSAID is present in said core;
  ii) said coating that does not release said NSAID unless the pH of the surrounding medium is 3.5 or higher surrounds said core; and
  iii) said acid inhibitor is in said one more layers outside said core.

13. The pharmaceutical composition of claim 12, wherein said one or more layers outside of said core do not contain NSAID and are not surrounded by an enteric coating.

14. The pharmaceutical composition of claim 13, wherein said unit dosage form is a bilayer tablet having an outer layer of said acid inhibitor and an inner core of said NSAID and wherein said outer layer of said tablet is surrounded by a non-enteric film coating that releases said acid inhibitor upon ingestion by patient.

15. The pharmaceutical composition of any one of claims 1 or 7–14, wherein said acid inhibitor is a proton pump inhibitor.

16. The pharmaceutical composition of claim 15, wherein said coating surrounding said core does not dissolve unless the pH of the surrounding medium is 4 or greater.

17. The pharmaceutical composition of claim 15, wherein said coating surrounding said core does not dissolve unless the pH of the surrounding medium is 5 or greater.

18. The pharmaceutical composition of any one of claims 7–14, wherein said acid inhibitor is an H2 blocker.

19. The pharmaceutical composition of claim 18, wherein said tablet has an inner core of said NSAID surrounded by a barrier coating that dissolves at a rate such that said NSAID is not released until the pH of the surrounding medium is 4 or greater.

20. The pharmaceutical composition of claim 18, wherein said tablet has an inner core of said NSAID surrounded by a barrier coating that dissolves at a rate such that said NSAID is not released until the pH of the surrounding medium is 5 or greater.

21. The pharmaceutical composition of claim 1, wherein said unit dosage form is a capsule.

22. A method of treating a patient for pain or inflammation, comprising administering to said patient the pharmaceutical composition of any one of claims 1–14.

23. The method of claim 22, wherein said pain or inflammation is due to either osteoarthritis or rheumatoid arthritis.

24. A method of treating a patient for pain or inflammation, comprising:
  (a) orally administering to said patient an acid inhibitor at a dose effective to raise the gastric pH of said patient to at least 3.5; and
  (b) orally administering to said patient an NSAID that is coated in a polymer that only dissolves at a pH of 3.5 or greater.

25. The method of claim 24, wherein said acid inhibitor is an H2 blocker.

26. The method of claim 25, wherein said H-2 blocker is selected from the group consisting of: cimetidine; ranitidine; ebrotidine; pabutidine; lafutidine; loxtidine and famotidine.

27. The method of claim 26, wherein said H2 blocker is famotidine administered at a dose of between 5 mg and 100 mg.

28. The method of claim 24, wherein said acid inhibitor is a proton pump inhibitor.

29. The method of claim 28, wherein said proton pump inhibitor is selected from the group consisting of: omeprazole, esomeprazole, lansoprazole, rabeprazole and pantoprazole.

30. The method of claim 29, wherein said proton pump inhibitor is pantoprazole administered at a dose of between 10 mg and 200 mg.

31. The method of any one of claims 24–30, wherein said NSAID is a COX-2 inhibitor selected from the group consisting of: celecoxib; rofecoxib; meloxicam; piroxicam; valdecoxib, parecoxib, etoricoxib, CS-502, JTE-522; L-745, 337; and NS398.

32. The method of any one of claims 24–30, wherein said NSAID is selected from the group consisting of: aspirin; acetaminophen; ibuprofen; flurbiprofen; ketoprofen; lornoxicam; naproxen; oxaprozin; etodolac; indomethacin; ketorolac; and nabumetone.

33. The method of claim 32, wherein said NSAID is naproxen administered at a dose of between 50 mg and 1500 mg.

34. The method of claim 33, wherein said naproxen is administered at a dose of between 200 mg and 600 mg.

35. The method of claim 24, wherein said acid inhibitor and said NSAID are delivered as part of a single dosage form providing for the coordinated release of therapeutic agents.

36. The method of claim 35, wherein said single dosage form is a bilayer tablet with an outer layer comprising an H2 blocker and an inner core comprising an NSAID.

37. A method of treating a patient for pain or inflammation, comprising:
  (a) orally administering to said patient an acid inhibitor at a dose effective to raise the gastric pH of said patient to at least 3.5; and
  (b) concurrently administering to said patient an NSAID that is coated in a polymer that dissolves at a rate such that said NSAID is not released until said gastric pH is at 3.5 or higher.

38. The method of claim 37, wherein said acid inhibitor is an H2 blocker.

39. The method of claim 38, wherein said H-2 blocker is selected from the group consisting of: cimetidine; ranitidine; ebrotidine; pabutidine; lafutidine; loxtidine and famotidine.

40. The method of claim 39, wherein said H2 blocker is famotidine administered at a dose of between 5 mg and 100 mg.

41. The method of claim 37, wherein said acid inhibitor is a proton pump inhibitor.

42. The method of claim 41, wherein said proton pump inhibitor is selected from the group consisting of: omeprazole, esomeprazole, lansoprazole, rabeprazole and pantoprazole.

43. The method of claim 42, wherein said proton pump inhibitor is pantoprazole administered at a dose of between 10 mg and 200 mg.

44. The method of any one of claims 37–43, wherein said NSAID is a COX-2 inhibitor selected from the group consisting of: celecoxib; rofecoxib; meloxicam; piroxicam; valdecoxib, parecoxib, etoricoxib, CS-502, JTE-522 L-745, 337; and NS398.

45. The method of any one of claims 37–43, wherein said NSAID is selected from the group consisting of: aspirin; acetaminophen; ibuprofen; flurbiprofen; ketoprofen; lornoxicam; naproxen; oxaprozin; etodolac; indomethacin; ketorolac; and nabumetone.

46. The method of claim 45, wherein said NSAID is naproxen administered at a dose of between 50 mg and 1500 mg.

47. The method of claim 46, wherein said naproxen is administered at a dose of between 200 mg and 600 mg.

48. The method of claim 47, wherein said acid inhibitor and said NSAID are delivered as part of a single dosage form providing for the coordinated release of therapeutic agents.

49. The method of claim 48, wherein said single dosage form is a bilayer tablet with an outer layer comprising an H2 blocker and an inner core comprising an NSAID.

50. A method of improving compliance in patients requiring frequent daily dosages of an acid inhibitor and an NSAID comprising administering said dosages in a coordinated unit dosage form in accordance with claim 1.

51. A method of treating a patient for pain or inflammation, comprising administering to said patient the pharmaceutical composition of claim 15.

52. The method of claim 51, wherein said pain or inflammation is due to either osteoarthritis or rheumatoid arthritis.

53. The pharmaceutical composition of any one of claims 5–11 wherein said unit dosage form is a multilayer tablet comprising a single core and one or more layers outside of said single core, wherein:

i) said NSAID is present in said core;
ii) said coating that does not release said NSAID unless the pH of the surrounding medium is 3.5 or higher surrounds said core; and
iii) said acid inhibitor is in said one more layers outside said core.

54. The pharmaceutical composition of claim 53, wherein said one or more layers outside of said core do not contain NSAID and are not surrounded by an enteric coating.

55. The pharmaceutical composition of claim 54, wherein said unit dosage form is a bilayer tablet having an outer layer of said acid inhibitor and an inner core of said NSAID and wherein said outer layer of said tablet is surrounded by a non-enteric film coating that, upon ingestion by a patient, releases said acid inhibitor into the stomach of said patient.

* * * * *

UNITED STATES PATENT AND TRADEMARK OFFICE
CERTIFICATE OF CORRECTION

| | |
|---|---|
| PATENT NO. | : 6,926,907 B2 |
| APPLICATION NO. | : 10/158216 |
| DATED | : August 9, 2005 |
| INVENTOR(S) | : John Plachetka |

It is certified that error appears in the above-identified patent and that said Letters Patent is hereby corrected as shown below:

In the first line of claim 1 line 1 in the issued patent, the word "dose" should be --dosage.-- Thus, the correct claim should read as follows:

Col. 20, Claim

1. A pharmaceutical composition in unit dosage form suitable for oral administration to a patient, comprising: (a) an acid inhibitor present in an amount effective to raise the gastric pH of said patient to at least 3.5 upon the administration of one or more of said unit dosage forms; (b) a non-steroidal anti-inflammatory drug (NSAID) in an amount effective to reduce or eliminate pain or inflammation in said patient upon administration of one or more of said unit dosage forms;

and wherein said unit dosage form provides for coordinated release such that:

i) said NSAID is surrounded by a coating that, upon ingestion of said unit dosage form by said patient, prevents the release of essentially any NSAID from said dosage form unless the pH of the surrounding medium is 3.5 or higher; ii) at least a portion of said acid inhibitor is not surrounded by an enteric coating and, upon ingestion of said unit dosage form by said patient, is released regardless of whether the pH of the surrounding medium is below 3.5 or above 3.5.

UNITED STATES PATENT AND TRADEMARK OFFICE
CERTIFICATE OF CORRECTION

PATENT NO. : 6,926,907 B2
APPLICATION NO. : 10/158216
DATED : August 9, 2005
INVENTOR(S) : John Plachetka It is certified that error appears in the above-identified patent and that said Letters Patent is hereby corrected as shown below:

Col. 21, Line 1 of claim 16 and 17 should refer to "any one of claims 12-14" and not to "claim 15." In addition, the phrase --wherein said acid inhibitor is a proton pump inhibitor-- should be included in 16 and 17. Thus, the claims should read as follows:

Col. 21

16. The pharmaceutical composition of any one of claims 12-14, wherein said acid inhibitor is a proton pump inhibitor and wherein said coating surrounding said core does not dissolve unless the pH of the surrounding medium is 4 or greater.

17. The pharmaceutical composition of any one of claims 12-14, wherein said acid inhibitor is a proton pump inhibitor and wherein said coating surrounding said core does not dissolve unless the pH of the surrounding medium is 5 or greater.

Col. 21, Line 1 of claims 19 and 20 should refer to "any one of claims 12-14" and not to "claim 18." In addition, the phrase --wherein said acid inhibitor is an H2 blocker-- should be included in 19 and 20. Thus, the claims should read as follows:

Col. 21

19. The pharmaceutical composition of any one of claims 12-14, wherein said acid inhibitor is an H2 blocker and wherein said tablet has an inner core of said NSAID surrounded by a barrier coating that dissolves at a rate such that said NSAID is not released until the pH of the surrounding medium is 4 or greater.

UNITED STATES PATENT AND TRADEMARK OFFICE
CERTIFICATE OF CORRECTION

PATENT NO. : 6,926,907 B2
APPLICATION NO. : 10/158216
DATED : August 9, 2005
INVENTOR(S) : John Plachetka

It is certified that error appears in the above-identified patent and that said Letters Patent is hereby corrected as shown below:

Col. 21

20. The pharmaceutical composition of any one of claims 12-14, wherein said acid inhibitor is an H2 blocker and wherein said tablet has an inner core of said NSAID surrounded by a barrier coating that dissolves at a rate such that said NSAID is not released until the pH of the surrounding medium is 5 or greater.

Signed and Sealed this

Twenty-fifth Day of December, 2007

JON W. DUDAS
*Director of the United States Patent and Trademark Office*